United States Patent [19]
Honda et al.

[11] Patent Number: 5,144,090
[45] Date of Patent: Sep. 1, 1992

[54] METHOD FOR PREPARING ACROLEIN OR METHACROLEIN

[75] Inventors: Tadatoshi Honda; Tokio Nagayama, both of Kanagawa; Nobuhiko Horiuchi, Yamaguchi; Jun Kitagawa, Yamaguchi; Kazunori Kawahara, Yamaguchi; Masami Murakami, Kanagawa, all of Japan

[73] Assignee: Mitsui Toatsu Chemicals, Inc., Tokyo, Japan

[21] Appl. No.: 711,032

[22] Filed: Jun. 6, 1991

[30] Foreign Application Priority Data

Jun. 6, 1990 [JP] Japan ................... 2-146296
Nov. 14, 1990 [JP] Japan ................... 2-306139
Nov. 14, 1990 [JP] Japan ................... 2-306141

[51] Int. Cl.⁵ ................. C07C 45/37; C07C 45/35
[52] U.S. Cl. ...................... 568/476; 568/469.9; 568/470; 568/471; 568/474; 568/475; 568/477; 568/478; 568/479; 568/480; 568/481
[58] Field of Search .......... 568/469.9, 470, 471, 568/474, 475, 476, 478, 479, 480, 477, 481

[56] References Cited

U.S. PATENT DOCUMENTS

| | | | |
|---|---|---|---|
| 3,972,920 | 8/1976 | Ishii et al. | 568/477 |
| 4,012,449 | 3/1977 | Shikakura et al. | 568/477 |
| 4,035,418 | 7/1977 | Okada et al. | 568/477 |
| 4,111,984 | 9/1978 | Ishii et al. | 568/476 |
| 4,111,985 | 9/1978 | Okada et al. | 568/477 |
| 4,219,670 | 8/1980 | Okada et al. | 568/477 |
| 4,306,090 | 12/1981 | Kirch et al. | 568/481 |
| 4,479,013 | 10/1984 | Khoobiar | 568/479 |
| 4,816,603 | 3/1989 | Oh-Kita et al. | 568/477 |
| 4,968,846 | 11/1990 | Kuragano et al. | 568/476 |

Primary Examiner—Werren B. Lone
Attorney, Agent, or Firm—Oblon, Spivak, McClelland, Maier & Neustadt

[57] ABSTRACT

A method for preparing acrolein or methacrolein comprises subjecting propylene, secondary propanol, isobutylene or tertiary butanol to gas phase catalytic oxidation with molecular oxygen in the presence of a catalyst represented by the following general formula (I):

$$Mo_a Bi_b Fe_c X_d Y_e Z_f O_g \qquad (I)$$

wherein X represents at least one element selected from the group consisting of Ni and Co; Y represents at least one element selected from the group consisting of K, Rb, Cs and Tl; and Z represents at least one element selected from the group consisting of Be, Mg, Ca, Sr, Ba, Ce, Ti, Zr, Nb, Cr, W, Mn, Cu, Ag, Zn, Cd, B, Al, Si, Ge, Sn, Pb, P, As, Sb, S, Se and Te; a, b, c, d, e, f and g each represents an atomic ratio of the corresponding element and when a is assumed to be 12, $b=0.1 \sim 10$, $c=0.1 \sim 20$, $d=2 \sim 20$, $e=0.01 \sim 2$, $f=0 \sim 4$ and g represents the number of oxygen atoms required for satisfying the valency requirement of the constituent elements, wherein the catalyst used is prepared by separately preparing solutions each of which contains the starting compound for the foregoing catalyst components, mixing these solutions within a short period of time, spray-drying the resulting mixture immediately after the mixing and then calcining the dried powder. A catalyst which further comprises 5 to 15% by weight of silica in addition to the foregoing composition is also used in the method. End products can be obtained in high conversion and selectivity through the use of the foregoing catalyst. Moreover, the catalyst is excellent in stability and has good reproducibility.

6 Claims, No Drawings

METHOD FOR PREPARING ACROLEIN OR METHACROLEIN

BACKGROUND OF THE INVENTION

1. Field of the Invention

The present invention relates to a method for preparing acrolein or methacrolein which comprises subjecting propylene, secondary propanol, isobutylene or tertiary butanol to gas phase catalytic oxidation with molecular oxygen.

2. Prior Art

Heretofore, there have been a variety of catalysts used in the preparation of acrolein or methacrolein through gas phase catalytic oxidation of propylene, secondary propanol, isobutylene or tertiary butanol with molecular oxygen. In particular, it has been known that catalysts which comprise, as essential components, Mo, Bi and Fe as well as at least one member selected from the group consisting of Ni and Co, and at least one member selected from the group consisting of K, Rb, Cs and Tl are effective for the aforementioned reaction and there have been proposed various such catalysts. For instance, in Japanese Unexamined Patent Publication (hereinafter referred to as "J.P. KOKAI") No. Sho 48-52713, a catalytic composition represented by the following general formula:

$$Co_aFe_bBi_cL_dH_eMo_fO_g$$

wherein L represents an element selected from the group consisting of P, As and B; H represents an element selected from the group consisting of K, Rb and Cs; and when f is assumed to be 12, a ranges from 2 to 15, b from 0.5 to 7, c from 0.1 to 4, d from 0 to 2, e from 0.01 to 1.0 and g is a value determined on the basis of the standard valencies of these constituent elements and calcined at a high temperature ranging from 650° C. to 1,000° C., is used as a catalyst for the gas phase catalytic oxidation reaction. If the catalyst is calcined at a high temperature of 650° C. or higher, the selectivity to end products would be enhanced, but the problem of a decrease in the catalytic activity arises. GB Pat. No. 1529384 discloses method in which two types of catalyst are employed, one of which comprises a coating catalyst obtained by attaching to an inert carrier a catalytic component represented by the following general formula:

$$A_aB_bFe_cBi_dMo_{12}O_x$$

wherein A represents an alkali metal, an alkaline earth metal, Sm, Ta, Tl, In, Ga, B, P, As, Sb or mixture thereof; B represents Ni, Co, Mg, Mn or mixture thereof; a=0~8, b=0~20, c=0.1~10, d=0.01~6 and x is the number of oxygen atoms required for satisfying the valency requirement of the constituent elements and the other of which is the second catalyst comprising the aforementioned catalytic component per se, and the patent also discloses that the temperature control of an exothermic reaction at an industrially effective high feed rate can be ensured only by arranging this catalytic system in a tube of a fixed bed reactor so that a reactant is first brought into contact with the first catalyst and then with the second catalyst. The patent further states that when a conventional compression-molded catalyst comprising the foregoing catalytic component per se is employed, the heat generation is too large to control the reaction. Furthermore, U.S. Pat. No. 4,511,671 discloses, as a catalyst for use in preparing methacrolein, a ring-like catalyst which comprises a catalytically active substance represented by the following general formula:

$$Mo_aW_bBi_cFe_dA_eB_fC_gD_hO_x$$

wherein A is a member selected from the group consisting of Ni and Co; B is a member selected from the group consisting of alkali metals, alkaline earth metals and thallium; C is a member selected from the group consisting of P, Te, Sb, Sn, Ce, Pb, Nb, Mn and Zn; D is a member selected from the group consisting of Si, Al, Ti and Zr; when a is assumed to be 12, b=0~10, c=0.1~10, d=0.1~20, e=2~20, f=0~10, g=0~4, h=0~30, and x is determined by the oxidized conditions of the constituent elements and also discloses that the usual catalysts in the form of tablets show reduction in their activity upon using over a long time period and thus suffer from a problem of the stability thereof.

As has been discussed above, the conventional catalysts are insufficient in catalyst properties such as activity, selectivity, stability and duration of life and hence there has been desired for the improvement of these catalyst in such properties. Moreover, the methods for preparing these catalysts are insufficient in reproducibility since the quality of the resulting catalysts differs from lot to lot and thus the improvement of these catalyst has also been desired from this standpoint.

SUMMARY OF THE INVENTION

Accordingly, an object of the present invention is to provide a method for preparing acrolein or methacrolein with a high conversion and selectivity through gas phase catalytic oxidation of propylene, secondary propanol, isobutylene or tertiary butanol with molecular oxygen.

Another object of the present invention is to provide a method for preparing a catalyst for use in the foregoing gas phase catalytic oxidation reaction, which is excellent in activity, selectivity to end products and stability.

A further object of the present invention is to provide a method for preparing a catalyst exhibiting a good activity, selectivity to end products and stability, which makes it possible to prepare the catalyst exhibiting an uniform property, i.e., free of deviation in properties from lot to lot and a good reproducibility.

The inventors have diligently studied the components, composition, method for preparation and shape of a catalyst used for preparing acrolein or methacrolein through gas phase catalytic oxidation of propylene, secondary propanol, isobutylene or tertiary butanol with molecular oxygen, in particular a catalyst comprising, as essential components, Mo, Bi and Fe as well as at least one element selected from Ni, Co and at least one element selected from K, Rb, Cs, Tl in order to develop such a catalyst that is excellent in activity, selectivity to acrolein or methacrolein and stability. As a result, they have found out (1) that if the catalyst is prepared by separately preparing solutions each of which contains starting compounds for the foregoing catalytic components, mixing these solutions within a short period of time without aging, spray-drying the resulting mixture immediately after the mixing to give dried powders and then preparing an intended catalyst from the dried powders, the resulting catalyst would have been greatly improved in the activity, selectivity to end products and stability, (2) that in case silica is used in addition to the above-mentioned catalytic components, the resulting catalyst would have been greatly improved in the activity, selectivity to (meth) acrolein and stability, if the content of silica is limited to a narrow range and the calcination temperature during the preparation of the catalyst is limited to a specific range and (3) that the activity, selectivity to end products and stability of the resulting catalyst can be greatly improved if the catalyst is formed into a spoked ring-like shape, as compared with those formed into a spherical, cylindrical or ring-like shape which has widely been used in this field, even if these catalyst having such shapes are formed from the starting powders of the same lot.

According to the present invention, there is provided a method for preparing (meth)acrolein which comprises subjecting propylene, secondary propanol, isobutylene or tertiary butanol to gas phase catalytic oxidation with molecular oxygen in the presence of a catalyst represented by the following general formula I:

$$Mo_aBi_bFe_cX_dY_eZ_fO_g \qquad (I)$$

wherein X represents at least one element selected from the group consisting of Ni and Co; Y represents at least one element selected from the group consisting of K, Rb, Cs and Tl; and Z represents at least one element selected from the group consisting of Be, Mg, Ca, Sr, Ba, Ce, Ti, Zr, Nb, Cr, W, Mn, Cu, Ag, Zn, Cd, B, Al, Si, Ge, Sn, Pb, P, As, Sb, S, Se and Te; a, b, c, d, e, f and g each represents an atomic ratio of the corresponding element and when a is assumed to be 12, $b=0.1\sim10$, $c=0.1\sim20$, $d=2\sim20$, $e=0.01\sim2$, $f=0\sim4$ and g represents the number of oxygen atoms required for satisfying the valency requirement of the constituent elements, characterized in that a catalytic composition obtained by separately preparing solutions each of which contains the starting compound for the foregoing catalytic components, mixing these solutions within a short period of time without aging, spray-drying the resulting mixture immediately after the mixing and then calcining the dried powders is used as said catalyst.

DETAILED DESCRIPTION OF THE INVENTION

The Mo-Bi-Fe composite oxide catalysts used in the method of the present invention have widely been used in the art as catalysts for oxidizing the allyl-position, but these catalysts have, in general, been prepared, for example as disclosed in U.S. Pat. No. 4,511,671 by a method which comprises preparing aqueous two or more solutions each containing starting compounds for the catalyst constituent components, mixing these solutions while dropwise adding one of the solutions to the remaining solution, concentrating the mixture to dryness under heating and stirring and then calcining the resulting dried product. On the contrary, the process of the present invention is characterized in that the catalyst is prepared by mixing these solutions in a short time as soon as possible, spray-drying the mixture immediately thereafter and then calcining the resulting powdery product.

In the conventional process of mixing the solutions while dropwise adding and concentrating the resulting mixture to dryness under heating and stirring, it is assumed that complicated reaction and phenomena such as dehydration-polymerization, nucleation, adsorption, precipitation and redissolution simultaneously take place in a liquid phase or solid phase. These reaction and phenomena are caused due to the facts that the rate of each elementary reaction is changed by various factors such as the concentration of the solutions to be mixed, the temperature, the pH value, the order of mixing, the speed of the dropwise addition, the stirring speed, the size and shape of the precipitation tank, the temperature hysteresis during heating and stirring, the stirring speed, the speed of concentration, and the bath temperature during the concentration, and as a result, the conditions for preparation of the catalysts are shifted so that this leads to the marked changes in the physicochemical properties of the resulting inorganic condensed-polymerized product and hence, the deviation in the quality of the resulting catalyst.

The basic technical idea of the method of the present invention is to complete the reaction within a very short time period for eliminating the occurrence of slow simultaneous-reactions in which the liquid phase is involved and for simplify the reaction as much as possible. More specifically, in the method of the present invention, the problems of the slow simultaneous-reactions and/or phenomena such as dehydration-polymerization reaction, adsorption and redissolution in which the liquid phase is involved are eliminated by mixing at least two solutions of the starting compounds which contain constituent components of the catalyst within a time as short as possible and immediately thereafter, spray-drying the mixture and further, the problems of hysteresis which is difficult to control is substantially eliminated by adopting the spray-drying process which makes it possible to quickly perform nucleation, dehydration and drying at one step.

The solutions each containing the starting compound for constituent components represented by the foregoing general formula (I) may be prepared according to any known method which has been commonly used in the art, for instance, according to the following method:

An appropriate molybdate such as ammonium molybdate is dissolved in pure water under heating and then at least one salt of an element selected from K, Rb, Cs and Tl such as a nitrate is added to the resulting solution to give a first starting solution. A compound of Fe, Co and/or Ni such as a nitrate is dissolved in pure water to give a second starting solution. A bismuth compound such as nitrate thereof is dissolved in pure water to form a third starting solution.

In the foregoing solutions, the corresponding starting compound included in each solution is combined with starting compound(s) which never cause such reaction and/or phenomena as dehydration-polymerization, nucleation, adsorption, precipitation and redissolution during preparing the starting solutions and storing the same. For this reason, the number of such solutions is in general two or more and it is not restricted to a specific number.

The catalyst of the present invention may optionally contain a compound of at least one element selected from the group consisting of Be, Mg, Ca, Sr, Ba, Ce, Ti, Zr, Nb, Cr, W, Mn, Cu, Ag, Zn, Cd, B, Al, Si, Ge, Sn, Pb, P, As, Sb, S, Se and Te as the component Z.

The compound as the component Z may be added to any one of the foregoing solutions so that a uniform solution can be obtained or a 4th solution may be separately formed therefrom.

The starting compounds for use in preparing the catalyst of the present invention are preferably those which can be decomposed into the corresponding oxides during the processes for preparing the catalyst. Examples of such compounds are nitrates such as cobalt nitrate, cesium nitrate, ferric nitrate and bismuth nitrate; ammonium salts; salts of organic acids such as cobalt acetate, ferric acetate and potassium acetate; hydroxides; oxides such as molybdenum trioxide; metallic acids; and ammonium salts of metallic acids such as ammonium molybdate.

In addition, an inorganic acid such as nitric acid is added to these solutions to adjust the pH value of the mixed solution obtained by mxing these solutions to 5 or lower. This is preferred for enhancing the reproducibility of the quality of the resulting catalyst since the dehydration-polymerization reaction can correspondingly be suppressed substantially.

It is also possible to add a thickening agent such as polyvinyl alcohol and methyl cellulose to these solutions in order to increase the viscosity of the solutions and to thus control the particle size of catalyst powders obtained after the spray-drying.

In the method of the present invention, at least two solutions containing the foregoing catalytic components are mixed within a time as short as possible and immediately thereafter, spray-dried.

As methods for mixing, there may be used, for instance, mixing by stirring, mixing by application of ultrasonics, or by means of a line mixer or static mixer, which are commonly adopted in the art. The mixing time is preferably as short as possible. The mixing time varies depending on the temperature during mixing, but in general the mixing operation is finished within several minutes and at longest several tens of minutes.

The temperature during mixing is not critical, but in general, around ordinary temperature.

The mixed solution is immediately spray-dried after the mixing. The method of and the conditions for the spray-drying are not also limited to specific ones and those commonly employed in the art can be used as such.

The powders obtained after the spray-drying are calcined, optionally formed into a desired shape and then fired at a temperature of not less than 400° C. and less than 650° C. for 1 to 20 hours.

In the method of the present invention, a catalyst which further contains silica in addition to the foregoing components may also be used. In this case, the catalyst comprises 85 to 95% by weight of the composition represented by the foregoing general formula (I) and 5 to 15% by weight of silica and the firing of this catalyst is carried out at a temperature of not less than 500° C. and less than 650° C. The content of silica in the catalyst is critical and the firing temperature is also critical.

As materials for silica, there may be used, for instance, silica sol, silica gel, silicic acid esters and silicates.

If the content of silica is less than 5% by weight, there is obtained only catalysts having a very low activity and selectivity to acrolein or methacrolein after calcination thereof at a temperature of not less than 500° C. and less than 650° C., while the catalysts obtained by calcinating at a temperature less than 500° C. have a desired level of activity and selectivity, but are insufficient in stability.

On the other hand, if it exceeds 15% by weight, the resulting catalyst has good stability, but has low selectivity to acrolein or methacrolein. If the content of silica is further increased, there are observed tendency of reducing not only the selectivity but also the activity.

Moreover, if the catalyst is calcined at a temperature of 650° C. or higher, all of the resulting catalysts have quite low activity and selectivity to acrolein or methacrolein.

The resulting catalysts are used in a fixed bed in the form of particles or a molded body, but they may also be used in a moving bed or a fluidized bed.

When they are used in the fixed bed as a molded body having a spoked ring-like shape, the activity, selectivity and stability of the catalyst are further improved as compared with those conventionally used shapes such as spherical or cylindrical shapes.

The spoked ring-shaped catalyst has an outer diameter ranging from 4 mm to 15 mm; a thickness of the ring ranging from 0.5 mm to 3 mm; a thickness of the spoke ranging from 0.5 to 3 mm; and a height of the shape ranging from 0.5 to 2 times the outer diameter of the ring. In addition, the number of the spokes is 2 or more and preferably 8 or less.

The reason why the spoked ring-shaped catalyst is specifically excellent in not only the initial performances but also the stability has not yet been clearly elucidated, but this seems to be attained, for instance, due to the facts that the physical outer surface area of the catalyst per unit packing volume is greater than those attained by the catalysts having spherical or cylindrical shapes which have widely been used conventionally, the degradation of the catalyst during packaging the same is low since the crushing strength of the catalyst particle is greater than those for the ring-like catalysts, the differential pressure during the reaction at practical height of catalyst packing is low, and further, since the reaction pressure can be reduced, side-reactions due to overoxidation during the partial oxidation reaction which is likewise involved in the present invention can be suppressed.

The gas phase catalytic oxidation reaction can be carried out by passing a mixed gas as the starting gas which comprises 1 to 10% by volume of propylene, secondary propanol, isobutylene or tertiary butanol, 3 to 20% by volume of molecular oxygen and 70 to 90% by volume of a diluent gas over the foregoing catalyst at a temperature ranging from 250° C. to 450° C. and a pressure ranging from ordinary pressure to 10 atm and at a space velocity ranging from 300 to 5,000/hr.

As the molecular oxygen, air is usually used, but pure oxygen may likewise be employed.

Examples of the diluent gases used are inert gases such as nitrogen gas and carbon dioxide gas. It is likewise possible to circulate a part Of the uncondensable gas included in the reaction gas mixture as such a diluent gas.

It is preferred to simultaneously use water vapor, as a part of the diluent gas, from the viewpoint of the improvement of the activity and selectivity of the catalyst. In this case, water vapor is in general added to the starting gas mixture in an amount of up to 60% by volume.

The present invention will hereinafter be explained in more detail with reference to the following non-limitative working Examples and Comparative Examples.

Example 1

A solution A was prepared by dissolving 1272 g of ammonium molybdate and then 43 g of cesium nitrate in 12,000 ml of water while heating and stirring the water and further adding 1110 g of a silica sol having a concentration of 20% by weight to the resulting solution.

Separately, a solution B was prepared by dissolving 1396 g of cobalt nitrate and 702 g of ferric nitrate in 1800 ml of water. Further, a solution C was prepared by dissolving 571.4 g of bismuth nitrate in an aqueous nitric acid solution containing 150 ml of a 60% nitric acid solution and 1,500 ml of water.

The resulting solutions A, B and C were supplied to a line mixer at flow rates of 1200 ml/min, 180 ml/min and 165 ml/min respectively, continuously mixed therein and the mixed solution discharged through an outlet of the line mixer was spray-dried as such. The resulting dried powders were calcined, formed into a cylindrical shape having a size of 5 mm (height)×5 mm (diameter) and then fired at 550° C. for 10 hours in the air to thus give a catalyst which comprised 90% by weight of a mixed oxide having an atomic ratio, Mo/Bi/Fe/Co/Cs, of 12/2.0/3.0/8.0/0.4 and 10% by weight of silica.

An amount of 40 ml of the resulting catalyst was charged into a ⅜ inch steel reactor tube and a reaction was performed using a starting gas mixture containing 6% by volume of isobutylene, 12% by volume of oxygen, 15% by volume of water vapor and the balance (67% by volume) of nitrogen, under the standard conditions, i.e., at a bath temperature of 350° C. and a space velocity of 1,000/hr to evaluate the initial performances of the resulting catalyst.

After the evaluation of the initial performances thereof, the reaction was further carried out under the forced deterioration conditions, i.e., at a bath temperature of 420° C. and a space velocity of 30,000/hr for 2 days using a starting gas mixture containing 10% by volume of isobutylene, 25% by volume of oxygen, 20% by volume of water vapor and the balance (45% by volume) of nitrogen. Thereafter, the reaction was conducted while the reaction conditions were brought back to the standard ones to thus evaluate the stability of the catalyst. The results obtained are listed in the following Table 1.

Example 2

In order to confirm the presence or absence of deviation in the performance of catalysts from lot to lot, a catalyst was prepared in the same manner as in Example 1 and the properties of the resulting catalyst were likewise examined. The results thus obtained are summarized in Table 1.

Examples 3 to 7

These Examples were carried out for making clear the influence of an aging step during preparing a catalyst on the performance of the resulting catalyst. First, solutions A, B and C having the same compositions as in Example 1 were prepared. Then the same procedures used in Example 1 were repeated except that, to the solution A, there were, in order, dropwise added the solutions B and C and that the resulting mixture was aged at 60° C. for 5 hours with stirring and then, spray-dried to obtain catalysts. The performance of the catalysts were evaluated in the same manner used in Example 1. The results obtained are listed in Table 1.

From the results obtained in the foregoing Examples, the following conclusions can be drawn.

The deviation in the properties of the catalysts from lot to lot was very slight when the catalyst was prepared by the method in which any aging step was not included. The initial performance and the properties obtained after the forced deterioration for the catalyst prepared by the method including no aging step were more excellent than those of the catalysts obtained through the aging step (comparison of the results observed in Examples 1 and 2 with those observed in Examples 3 to 7).

Examples 8 to 11

There were prepared catalysts comprising an oxide mixture having the corresponding atomic ratio as listed in Table 1 and silica in the same manner as in Example 1 and likewise, the performances of the resulting catalysts were evaluated. The results obtained are listed in Table 1.

Comparative Examples 1 to 8

Catalysts were prepared using oxide mixtures each having the corresponding atomic ratio as listed in Table 1 and silica in the same manner as in Example 3, provided that the firing temperature was changed to those shown in Table 1.

The performance of the resulting catalysts was evaluated in the same manner as in Example 1. The results obtained are listed in Table 1.

The following conclusions can be drawn from the results observed in the foregoing Examples and Comparative Examples:

If the content of silica is less than 5% by weight, the initial performance (both activity and selectivity to methacrolein) of the resulting catalyst is insufficient when the catalyst was fired at a temperature ranging from 500° C. to 650° C. (see Comparative Example 1).

The catalyst which was fired at a temperature of 500° C. or lower shows the desired initial performance, but is insufficient in the stability (see Comparative Example 2).

The catalyst having a silica content of more than 15% by weight has good stability, but the selectivity to methacrolein among the initial quality is low (see Comparative Example 3).

Moreover, as the silica content increases, the reduction in not only the selectivity to methacrolein but also the activity becomes conspicuous (see Comparative Example 4).

When the firing temperature exceeds 650° C., the activity and the selectivity of any catalysts to methacrolein were lowered (see Comparative Examples 5 to 8).

Example 12

A catalyst was prepared using an oxide mixture having an atomic ratio as listed in Table 1 and silica in the same manner as in Example 1. The performance of the catalyst was likewise evaluated in the same manner as in Example 1 except that propylene was substituted for the isobutylene in the starting gas mixture and that the reactor bath temperature was changed to 320° C. The results obtained are listed in Table 1.

Examples 13 to 17

Catalysts were prepared using oxide mixtures each having an atomic ratio as listed in Table 1 and silica in the same manner as in Example 1, provided that the catalysts were formed into spoked ring-like shapes having 5 mm each of height and diameter, a number of spokes of 2 and 1 mm each of thicknesses of the ring and spokes according to a compression molding method. The performance of the resulting catalysts was likewise evaluated in the same manner as in Example 1. The results obtained are listed in the following Table 1.

Example 18

This Example was carried out for making clear the influence of the size of the spoked ring-shaped catalyst on the performance of the resulting catalyst. The same procedures as in Example 13 were repeated using the catalyst powder of the same lot as in Example 13 to form a spoked ring-shaped catalyst having 2 spokes and a diameter of 20 mm. The performance of the resulting catalyst was likewise evaluated in the same manner as in Example 1. The results obtained are listed in Table 1.

Example 19

This Example was carried out for comparing the performance of the spoked ring-shaped catalyst with that for the ring-shaped catalyst. The same procedures as in Example 13 were repeated using the catalyst powder of the same lot as in Example 13 to form a ring-shaped catalyst having 5 mm each of diameter and height and a thickness of the ring of 1 mm. The performance of the resulting catalyst was likewise evaluated in the same manner as in Example 1. The results obtained are listed in Table 1.

Example 20

The same procedures used in Example 1 were repeated to form a catalyst and the performance of the resulting catalyst was likewise evaluated in the same method as in Example 1, provided that the starting gas mixture used for the reaction comprised 6% by volume of tertiary butanol, 12% by volume of oxygen, 9% by volume of water vapor and the balance of nitrogen. The results thus obtained are summarized in the following Table 1.

Comparative Example 9

The same procedures used in Example 19 except that the aging of the precipitates was carried out in the same manner as in Example 3. The results thus obtained are summarized in the following Table 1.

The following conclusions can be drawn from the results of the foregoing Examples:

The initial activity and selectivity as well as the performances observed after the forced deterioration of the spoked ring-shaped catalyst were more excellent than those for a cylindrical catalyst having a diameter equal to that for the former (comparison between Example 1 and Example 13).

The initial activity and selectivity as well as the performance observed after the forced deterioration of the spoked ring-shaped catalyst were more excellent than those for a cylindrical catalyst having a composition equal to that for the former (comparison between Examples 8 to 11 and Examples 13 to 17).

As has been discussed above in detail, there can be prepared catalysts having a high activity and an excellent selectivity to acrolein or methacrolein and stability with good reproducibility.

In addition, the activity, selectivity to acrolein or methacrolein and stability of the catalysts can be further enhanced by forming them into a spoked ring-like shape.

TABLE 1

| Ex. No. | Composition of Catalyst (atomic ratio) | | | | | | Content of Silica: wt % | Shape of Catalyst | Catalyst Size | | Calcination Temp. (°C.) | Initial Performances (%) | | Performances After Forced Deterioration | |
|---|---|---|---|---|---|---|---|---|---|---|---|---|---|---|---|
| | Mo | Bi | Fe | X | Y | Z | | | OD: mm | Thick: mm | | Conversion | Selectivity | Conversion (%) | Selectivity (%) |
| 1 | 12 | 2.0 | 3.0 | Co 8.0 | Cs 0.4 | — | 10 | cylindrical | 5 | | 550 | 98.2 | 87.1 | 98.2 | 87.0 |
| 2 | 12 | 2.0 | 3.0 | Co 8.0 | Cs 0.4 | — | 10 | cylindrical | 5 | | 550 | 98.3 | 87.0 | 98.1 | 87.2 |
| 3 | 12 | 2.0 | 3.0 | Co 8.0 | Cs 0.4 | — | 10 | cylindrical | 5 | | 550 | 98.1 | 86.4 | 98.0 | 86.9 |
| 4 | 12 | 2.0 | 3.0 | Co 8.0 | Cs 0.4 | — | 10 | cylindrical | 5 | | 550 | 98.8 | 85.9 | 98.0 | 84.9 |
| 5 | 12 | 2.0 | 3.0 | Co 8.0 | Cs 0.4 | — | 10 | cylindrical | 5 | | 550 | 98.2 | 83.4 | 97.0 | 84.5 |
| 6 | 12 | 2.0 | 3.0 | Co 8.0 | Cs 0.4 | — | 10 | cylindrical | 5 | | 550 | 97.9 | 84.1 | 97.1 | 84.7 |
| 7 | 12 | 2.0 | 3.0 | Co 8.0 | Cs 0.4 | — | 10 | cylindrical | 5 | | 550 | 98.0 | 84.9 | 97.0 | 83.4 |
| 8 | 12 | 2.0 | 3.0 | Co 8.0 | Cs 0.4 | Cu 0.5 | 10 | cylindrical | 5 | | 550 | 98.0 | 85.1 | 97.8 | 85.4 |
| 9 | 12 | 2.2 | 2.2 | Ni 5.8 | Cs 0.4 | — | 10 | cylindrical | 5 | | 550 | 98.1 | 85.9 | 97.8 | 85.1 |
| 10 | 12 | 2.2 | 2.6 | Ni 5.8 | Cs 0.5 | W 0.5 | 10 | cylindrical | 5 | | 590 | 98.0 | 85.5 | 97.7 | 85.8 |
| 11 | 12 | 2.0 | 3.0 | Co 8.0 | Cs 0.7 | — | 5 | cylindrical | 5 | | 550 | 95.4 | 83.2 | 94.8 | 84.1 |
| 12 | 12 | 2.2 | 3.0 | Co 8.0 | K 0.1 | — | 10 | cylindrical | 5 | | 550 | 98.7 | 91.2 | 98.4 | 91.8 |
| 13 | 12 | 2.0 | 3.0 | Co 8.0 | Cs 0.4 | — | 10 | 2 spokes | 5 | 1 | 550 | 99.5 | 88.7 | 99.1 | 88.9 |
| 14 | 12 | 2.0 | 3.0 | Co 8.0 | Cs 0.4 | Cu 0.5 | 10 | 2 spokes | 5 | 1 | 550 | 99.7 | 87.6 | 98.8 | 86.8 |
| 15 | 12 | 2.2 | 2.2 | Ni 5.8 | Cs 0.4 | — | 10 | 2 spokes | 5 | 1 | 550 | 99.5 | 87.2 | 98.9 | 86.8 |
| 16 | 12 | 2.2 | 2.6 | Ni 5.8 | Cs 0.5 | W 0.5 | 10 | 2 spokes | 5 | 1 | 550 | 98.9 | 87.4 | 98.5 | 86.7 |
| 17 | 12 | 2.0 | 3.0 | Co 8.0 | Cs 0.7 | — | 5 | 2 spokes | 5 | 1 | 550 | 98.4 | 87.3 | 97.9 | 86.9 |
| 18 | 12 | 2.0 | 3.0 | Co 8.0 | Cs 0.4 | — | 10 | 2 spokes | 20 | 1 | 550 | 96.5 | 86.5 | 96.1 | 86.4 |
| 19 | 12 | 2.0 | 3.0 | Co 8.0 | Cs 0.4 | — | 10 | ring | 5 | 1 | 550 | 98.8 | 87.8 | 98.3 | 87.2 |
| 20 | 12 | 2.0 | 3.0 | Co 8.0 | Cs 0.4 | — | 10 | cylindrical | 5 | | 550 | 98.1 | 86.9 | 98.0 | 86.8 |
| 1* | 12 | 2.0 | 3.0 | Co 8.0 | Cs 0.4 | — | 0 | cylindrical | 5 | | 550 | 80.5 | 60.9 | 69.5 | 57.1 |
| 2* | 12 | 2.0 | 3.0 | Co 8.0 | Cs 0.4 | — | 0 | cylindrical | 5 | | 480 | 98.1 | 84.8 | 84.4 | 72.1 |
| 3* | 12 | 2.0 | 3.0 | Co 8.0 | Cs 0.4 | — | 20 | cylindrical | 5 | | 550 | 96.1 | 70.8 | 95.0 | 69.3 |
| 4* | 12 | 2.0 | 3.0 | Co 8.0 | Cs 0.4 | — | 40 | cylindrical | 5 | | 550 | 81.4 | 69.3 | 80.8 | 66.4 |
| 5* | 12 | 2.0 | 3.0 | Co 8.0 | Cs 0.7 | — | 5 | cylindrical | 5 | | 680 | 73.9 | 71.6 | 73.2 | 68.4 |
| 6* | 12 | 2.0 | 3.0 | Co 8.0 | Cs 0.4 | Cu 0.5 | 10 | cylindrical | 5 | | 680 | 70.9 | 67.2 | 69.6 | 63.9 |
| 7* | 12 | 2.2 | 2.2 | Ni 5.8 | Cs 0.4 | — | 20 | cylindrical | 5 | | 680 | 77.7 | 63.8 | 75.4 | 62.6 |
| 8* | 12 | 2.2 | 2.6 | Ni 5.8 | Cs 0.5 | W 0.5 | 20 | cylindrical | 5 | | 680 | 80.2 | 70.6 | 76.3 | 68.9 |
| 9* | 12 | 2.0 | 3.0 | Co 8.0 | Cs 0.4 | — | 10 | ring | 5 | 1 | 550 | 99.1 | 82.3 | 98.8 | 82.0 |

OD: Outer diameter
*Comparative Example

We claim:

1. A method for preparing acrolein or methacrolein which comprises subjecting propylene, secondary propanol, isobutylene or tertiary butanol to gas phase catalytic oxidation with molecular oxygen in the presence of a catalyst represented by the following general formula (I):

$$Mo_aBi_bFe_cX_dY_eZ_fO_z \qquad (I)$$

wherein X represents at least one element selected from the group consisting of Ni and Co; Y represents at least one element selected from the group consisting of K, Rb, Cs and Tl; and Z represents at least one element selected from the group consisting of Be, Mg, Ca, Sr, Ba, Ce, Ti, Zr, Nb, Cr, W, Mn, Cu, Ag, Zn, Cd, B, Al, Si, Ge, Sn, Pb, P, As, Sb, S, Se and Te; a, b, c, d, e, f and g each represents an atomic ratio of the corresponding element and when a is 12, $b = 0.1 \sim 10$, $c = 0.1 \sim 20$, $d = 2 \sim 20$, $e = 0.01 \sim 2$, $f = 0 \sim 4$ and g represents the number of oxygen atoms required for satisfying the valency requirement of the constituent elements, method being characterized in using a catalytic composition obtained by separately preparing solutions each of which contains the starting compound for the foregoing catalyst components, mixing these solutions within a short period of time without aging, spray-drying the resulting mixture immediately after the mixing and then calcining the dried powders.

2. The method as set forth in claim 1 wherein the temperature for calcination of the catalyst is not less than 400° C. and less than 650° C.

3. The method as set forth in claim 1 wherein, in the preparation of the catalyst, an inorganic acid is added to the solution of the starting compound to adjust the pH value of the mixed solution to 5 or lower.

4. The method as set forth in claim 1 wherein, in the preparation of the catalyst, the starting compound included in each solution is combined with starting compound(s) which avoid dehydration-polymerization, nucleation, adsorption, precipitation and redissolution during preparing the starting solutions and storing them.

5. A method for preparing acrolein or methacrolein which comprises subjecting propylene, secondary propanol, isobutylene or tertiary butanol to gas phase catalytic oxidation with molecular oxygen in the presence of a catalyst represented by the following general formula (I):

$$Mo_aBi_bFe_cX_dY_eZ_fO_g \qquad (I)$$

wherein X represents at least one element selected from the group consisting of Ni and Co; Y represents at least one element selected from the group consisting of K, Rb, Cs and Tl; and Z represents at least one element selected from the group consisting of Be, Mg, Ca, Sr, Ba, Ce, Ti, Zr, Nb, Cr, W, Mn, Cu, Ag, Zn, Cd, B, Al, Si, Ge, Sn, Pb, P, As, Sb, S, Se and Te; a, b, c, d, e, f and g each represents an atomic ratio of the corresponding element and when a is 12, $b = 0.1 \sim 10$, $c = 0.1 \sim 20$, $d = 2 \sim 20$, $e = 0.01 \sim 2$, $f = 0 \sim 4$ and g represents the number of oxygen atoms required for satisfying the valency requirement of the constituent elements, said method being characterized in using a catalytic composition obtained by calcining a mixture comprising 85 to 95% by weight of the composition represented by the foregoing general formula (I) and 5 to 15% by weight of silica at a temperature of not less than 500° C. and less than 650° C.

6. The method as set forth in claim 1 or 5 wherein the catalyst has a spoked ring-like shape.

* * * * *